United States Patent [19]

Shimada et al.

[11] 4,150,025
[45] Apr. 17, 1979

[54] NOVEL QUINOLINE DERIVATIVES

[75] Inventors: Keizo Shimada, Hino; Toshiaki Harada; Masahiro Koga, both of Iwakuni, all of Japan

[73] Assignee: Teijin Limited, Japan

[21] Appl. No.: 767,635

[22] Filed: Feb. 10, 1977

[30] Foreign Application Priority Data

Feb. 17, 1976 [JP] Japan .................................. 51-15455
Jun. 25, 1976 [JP] Japan .................................. 51-74394
Sep. 28, 1976 [JP] Japan .................................. 51-115370
Oct. 7, 1976 [JP] Japan .................................. 51-119878
Oct. 25, 1976 [JP] Japan .................................. 51-127343

[51] Int. Cl.$^2$ .................... C09B 25/00; C07D 401/04
[52] U.S. Cl. .............................. 546/99; 106/288 Q; 8/1 D; 260/37 P; 546/167
[58] Field of Search ...... 260/287 F, 287 CE, 289 QP, 260/281 NH

[56] References Cited

U.S. PATENT DOCUMENTS

| | | | |
|---|---|---|---|
| 3,622,583 | 11/1971 | Dehnert | 260/287 R |
| 3,788,810 | 1/1974 | Kalz | 8/162 R |
| 4,067,870 | 1/1978 | Shimada et al. | 260/287 F |

OTHER PUBLICATIONS

Gething, B., et al, J. Chem. Soc., (1961), 1574–1576.
Pratt, D., et al., J. Am. Chem. Soc., 40, (1918), p. 254.

*Primary Examiner*—Paul M. Coughlan, Jr.
*Assistant Examiner*—Lisa Jones
*Attorney, Agent, or Firm*—Wenderoth, Lind & Ponack

[57] ABSTRACT

A compound of the formula

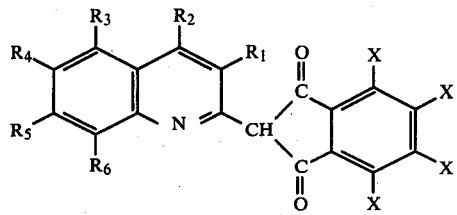

wherein $R_1$ represents a hydrogen atom or a lower alkyl group; $R_2$ and $R_5$, independently from each other, represent a hydrogen atom, a halogen atom or a lower alkyl group; one of $R_3$ and $R_4$ represents an imido group of the formula

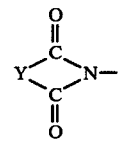

in which Y represents a 1,2-phenylene, 1,2-naphthylene, 2,3-naphthylene or 1,8-naphtylene group optionally containing at least one substituent, and the other represents a hydrogen atom, a halogen atom or a lower alkyl group; $R_6$ represents a hydrogen atom, a halogen atom, a lower alkyl group or a lower alkoxy group; and X represents a halogen atom; with the proviso that when $R_3$ represents the imido group, $R_2$ represents a hydrogen or halogen atom. This compound can be prepared by reacting a corresponding quinaldine derivative with a tetrahalophthalic acid or a reactive derivative thereof. A yellow organic pigment comprising this compound as a coloring ingredient is useful for coloring polymeric materials.

5 Claims, No Drawings

NOVEL QUINOLINE DERIVATIVES

This invention relates to quinoline derivatives, and more specifically, to novel quinoline derivatives, a process for their preparation, and their use as coloring agents.

A number of quinoline derivatives, particularly quinophthalone compounds, have been known heretofore. For example, U.S. Pat. No. 3,622,583 suggests compounds of the following formula

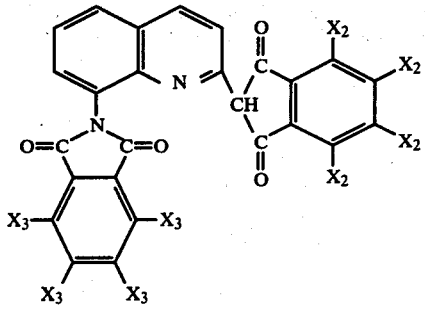

wherein $X_2$ and $X_3$, independently from each other, represent a chlorine or bromine atom, as yellow dyes. These quinoline derivatives suggested heretofore do not possess sufficient thermal stability and weatherability, and suffer from a defect of discoloration when used in the melt shaping of polymeric materials, for example.

It is an object of this invention to provide novel quinoline derivatives having superior thermal stability, weatherability, migration resistance and resistance to solvents.

Another object of this invention is to provide a process for preparing novel quinoline derivatives having superior thermal stability, weatherability, migration resistance and resistance to solvents.

Still another object of this invention is to provide yellow pigments having superior thermal stability, weatherability, migration resistance and resistance to solvents.

Still another object of this invention is to provide polymeric materials colored by these pigments.

The other objects and features of the present invention will become apparent from the following description.

According to this invention, there is provided a compound of the formula

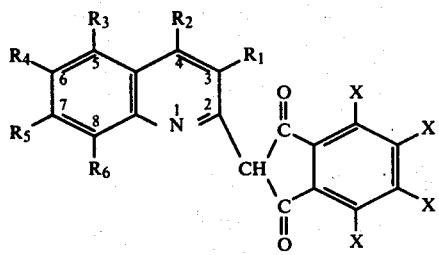

(I)

wherein $R_1$ represents a hydrogen atom or a lower alkyl group; $R_2$ and $R_5$, independently from each other, represent a hydrogen atom, a halogen atom or a lower alkyl group; one of $R_3$ and $R_4$ represents an imido group of the formula

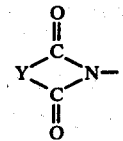

in which Y represents a 1,2-phenylene, 1,2-naphthylene, 2,3-naphthylene or 1,8-naphthylene group optionally having at least one substituent, and the other represents a hydrogen atom, a halogen atom or a lower alkyl group; $R_6$ represents a hydrogen atom, a halogen atom, a lower alkyl group or a lower alkoxy group; and X represents a halogen atom; with the proviso that when $R_3$ represents the imido group, $R_2$ represents a hydrogen or halogen atom.

In the present specification and the appended claims, the term "lower alkyl group" denotes a straightchain or branched-chain saturated aliphatic hydrocarbon group containing up to 5, preferably 1 to 3, carbon atoms, and includes, for example, methyl, ethyl, n- or iso-propyl, n-, iso-, sec- or tert-butyl, n- or neo-pentyl, and isoamyl. The methyl and ethyl groups are especially preferred.

The term "lower alkoxy group" denotes a saturated aliphatic hydrocarbyloxy group containing up to 5, preferably 1 to 3, carbon atoms, with the alkyl moiety being of straight chain or branched chain, and includes, for example, methoxy, ethoxy, n- or iso-propoxy, n-, iso-, sec- or tertbutoxy, and n-pentoxy. The methoxy and ethoxy groups, especially the former, are preferred.

The term "halogen atom" includes chlorine, bromine, fluorine and iodine atoms. Especially, chlorine and bromine atoms are preferred.

Y in the imido group is a 1,2-phenylene, 1,2-naphthylene, 2,3-naphthylene or 1,8-naphthylene group which may contain one or more substituents on the benzene or naphthalene nucleus. Ordinary substituents seen in the pigment and dye fields can be used, and examples include halogen atoms, lower alkyl groups, lower alkoxy groups, and arylsulfonyl groups such as benzenesulfonyl, p-toluenesulfonyl, p-chlorobenzenesulfonyl or p-bromobenzenesulfonyl. The halogen atoms are especially preferred. The number of such substituents that may be present is 1 to 6, preferably 1 to 4. When the number is 2 or more, the substituents may be identical to or different from each other. Specific examples of Y are 1,2-phenylene, monochloro(or monobromo)-1,2-phenylene, dichloro(or dibromo)-1,2-phenylene, tetrachloro(or tetrabromo)-1,2-phenylene, 1,8-naphthylene, 3(or 4)-chloro-1,8-naphthylene, 3(or 4)-bromo-1,8-naphthylene, hexabromo-1,8-naphthylene, 2,3-naphthylene, 5,8-dibromo-2,3-naphthylene, 5,6,7,8-tetrabromo-2,3-naphthylene, 1,2-naphthylene, and benzenesulfonyl-2,3-naphthylene. Solely from an economical viewpoint, 1,2-phenylene groups optionally having 1 to 4 halogen atoms, particularly 1,2-phenylene, tetrachloro-1,2-phenylene and tetrabromo-1,2-phenylene, are preferred.

The imido group can be present in either one of the 5- or 6-position of the quinoline nucleus of the quinoline derivative of formula (I). In this case, a halogen atom or a lower alkyl group can be present in the other of 5- or 6-position, but preferably the other position is unsubstituted. It has been found that compounds of formula (I) in which the imido group is present at the 5-position (that is, $R_3$ represents the imido group) generally have better weatherability. Accordingly, compounds of formula (I) wherein $R_3$ is the imido group are a group of especially preferred compounds in the present invention.

The substituent $R_6$ at the 8-position of the quinoline derivative of formula (I) represents a hydrogen atom, a halogen atom, a lower alkyl group or a lower alkoxy group, and it is especially advantageous that $R_6$ is other than hydrogen.

According to the invention, it has been found that compounds of formula (I) in which $R_6$ is a halogen atom, especially chlorine or bromine, have improved weatherability over compounds of formula (I) in which $R_6$ is other than halogen within the above definition. Thus, the compounds of formula (I) in which $R_6$ is a halogen atom, especially chlorine or bromine, are another group of preferred compounds in the present invention.

The compounds of formula (I) provided by the present invention can form tautomeric structures schematically shown below.

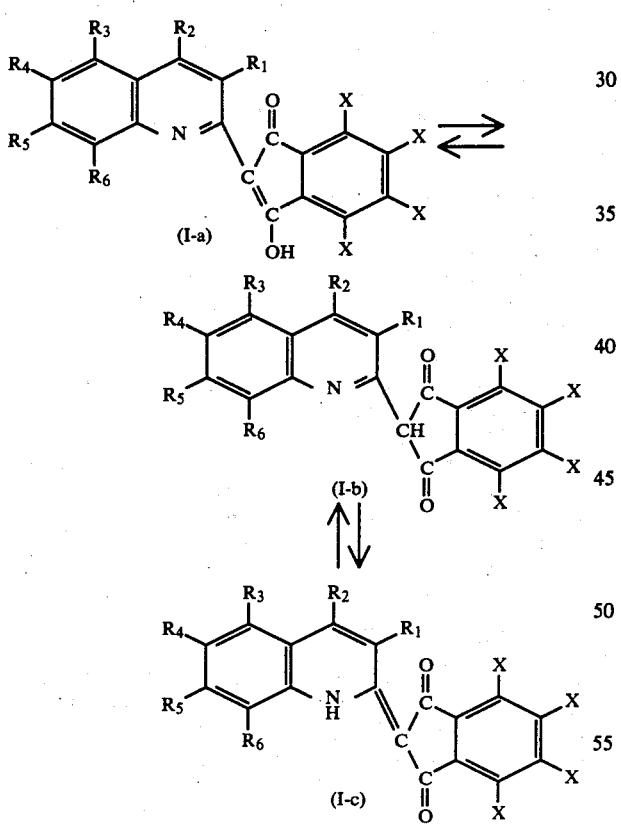

It is to be understood that in the present specification and the appended claims, the structural formula (I) is meant to represent all of the tautomeric structures of formulae (I-a), (I-b) and (I-c).

Of the compounds of formula (I) provided by the present invention, preferred species are those of the formula

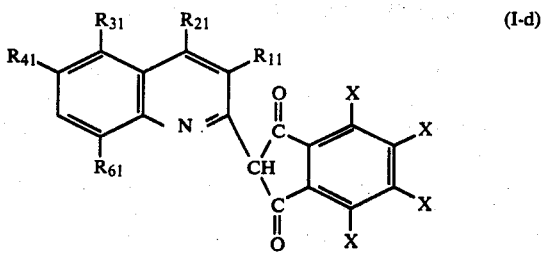

wherein $R_{11}$ and $R_{21}$, independently from each other, represent a hydrogen atom or a lower alkyl group; one of $R_{31}$ and $R_{41}$ represents an imido group of the formula

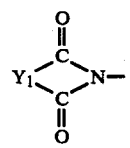

in which $Y_1$ represents a 1,2-phenylene, 1,2-naphthylene, 2,3-naphthylene or 1,8-naphthylene group optionally substituted by 1 to 6, preferably 1 to 4, halogen atoms, and the other represents a hydrogen atom; $R_{61}$ represents a halogen atom, a lower alkyl group or a lower alkoxy group; and X represents a halogen atom; with the proviso that when $R_{31}$ represents the imido group, $R_{21}$ represents a hydrogen atom. More preferred compounds of formula (I) in the most preferred group are expressed by the formula

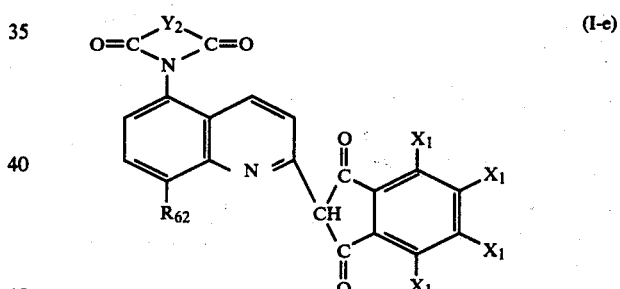

wherein $R_{62}$ represents a chlorine or bromine atom, an alkyl group containing 1 to 3 carbon atoms or an alkoxy group containing 1 to 3 carbon atoms; $Y_2$ represents a 1,2-phenylene, 1,2-naphthylene, 2,3-naphthylene or 1,8-naphthylene group optionally substituted by 1 to 4 chlorine or bromine atroms; and $X_1$ represents a chlorine or bromine atom. Another preferred group of compounds of formula (I) are expressed by the formula

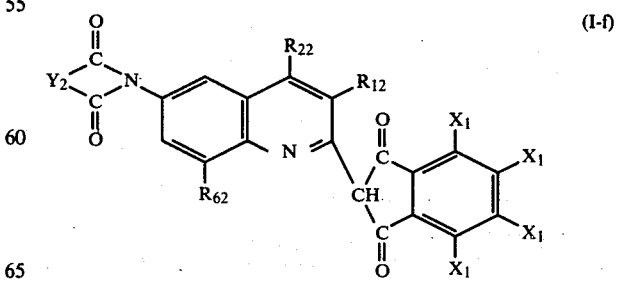

wherein $R_{12}$ and $R_{22}$, independently from each other, represent a hydrogen atom or an alkyl group containing 1 to 3 carbon atoms; $R_{62}$ represents a chlorine or bromine atom, an alkyl group containing 1 to 3 carbon atoms, or an alkoxy group containing 1 to 3 carbon atoms; $Y_2$ represents a 1,2-phenylene, 1,2-naphthylene, 2,3-naphthylene or 1,8-naphthylene group optionally substituted by 1 to 4 chlorine or bromine atoms; and $X_1$ represents a chlorine or bromine atom. Typical examples of the compounds of formula (I), (I-d), (I-e) or (I-f) are listed below.

(1) 4,5,6,7-tetrachloro(or tetrabromo)-2-[8-chloro-5(or 6)-tetrachloro(or tetrabromo)phthalimido-2-quinolinyl]-1,3-indandione, (2) 4,5,6,7-tetrachloro(or tetrabromo)-2-[8-bromo-5(or 6)-tetrachloro(or tetrabromo)phthalimido-2-quinolinyl]-1,3-indandione, (3) 4,5,6,7-tetrachloro(or tetrabromo)-2-[8-methyl-5(or 6)-tetrachloro(or tetrabromo)phthalimido-2-quinolinyl]-1,3-indandione, (4) 4,5,6,7-tetrachloro(or tetrabromo)-2-[8-ethyl-5(or 6)-tetrachloro(or tetrabromo)phthalimido-2-quinolinyl[-1,3-indandione, (5) 4,5,6,7-tetrachloro(or tetrabromo)-2-[8-methoxy-5(or 6)-tetrachloro(or tetrabromo)phthalimido-2-quinolinyl]-1,3-indandione, (6) 4,5,6,7-tetrachloro(or tetrabromo)-2-[8-ethoxy-5(or 6)-tetrachloro(or tetrabromo)phthalimido-2-quinolinyl]-1,3-indandione, (7) 4,5,6,7-tetrachloro(or tetrabromo)-2-[8-chloro-5(or 6)-phthalimido-2-quinolinyl]-1,3-indandione, (8) 4,5,6,7-tetrachloro(or tetrabromo)-2-[8-bromo-5(or 6)-phthalimido-2-quinolinyl]-1,3-indandione, (9) 4,5,6,7-tetrachloro(or tetrabromo)-2-[8-methyl-5(or 6)-phthalimido-2-quinolinyl]-1,3-indandione,

(10) 4,5,6,7-tetrachloro(or tetrabromo)-2-[8-ethyl-5(or 6)-phthalimido-2-quinolinyl]-1,3-indandione,

(11) 4,5,6,7-tetrachloro(or tetrabromo)-2-[8-methoxy-5(or 6)-phthalimido-2-quinolinyl]-1,3-indandione,

(12) 4,5,6,7-tetrachloro(or tetrabromo)-2-[8-ethoxy-5(or 6)-phthalimido-2-quinolinyl]-1,3-indandione,

(13) 4,5,6,7-tetrachloro(or tetrabromo)-2-[8-chloro-5(or 6)-naphthalimido-2-quinolinyl]-1,3-indandione,

(14) 4,5,6,7-tetrachloro(or tetrabromo)-2-[8-bromo-5(or 6)-naphthalimido-2-quinolinyl]-1,3-indandione,

(15) 4,5,6,7-tetrachloro(or tetrabromo)-2-[8-methyl-5(or 6)-naphthalimido-2-quinolinyl]-1,3-indandione,

(16) 4,5,6,7-tetrachloro(or tetrabromo)-2-[8-ethyl-5(or 6)-naphthalimido-2-quinolinyl]-1,3-indandione,

(17) 4,5,6,7-tetrachloro(or tetrabromo)-2-[8-methoxy-5(or 6)-naphthalimido-2-quinolinyl]-1,3-indandione,

(18) 4,5,6,7-tetrachloro(or tetrabromo)-2-[8-ethoxy-5(or 6)-naphthalimido-2-quinolinyl]-1,3-indandione,

(19) 4,5,6,7-tetrachloro(or tetrabromo)-2-{8-chloro-5(or 6)-[3(or 4)-bromo(or chloro)-naphthalimido]-2-quinolinyl}-1,3-indandione,

(20) 4,5,6,7-tetrachloro(or tetrabromo)-2-{8-bromo-5(or 6)-[3(or 4)-bromo(or chloro)-naphthalimido]-2-quinolinyl}-1,3-indandione,

(21) 4,5,6,7-tetrachloro(or tetrabromo)-2-{8-methyl-5(or 6)-[3(or 4)-bromo(or chloro)-naphthalimido]-2-quinolinyl}-1,3-indandione,

(22) 4,5,6,7-tetrachloro(or tetrabromo)-2-{8-ethyl-5(or 6)-[3(or 4)-bromo(or chloro)-naphthalimido]-2-quinolinyl}-1,3-indandione,

(23) 4,5,6,7-tetrachloro(or tetrabromo)-2-{8-methoxy-5(or 6)-[3(or 4)-bromo(or chloro)-naphthalimido]-2-quinolinyl}-1,3-indandione,

(24) 4,5,6,7-tetrachloro(or tetrabromo)-2-{8-ethoxy-5(or 6)-[3(or 4)-bromo(or chloro)naphthalimido]-2-quinolinyl}-1,3-indandione,

(25) 4,5,6,7-tetrachloro(or tetrabromo)-2-{8-chloro-5(or 6)-[5,8-dibromonaphthalene-2,3-dicarboximido]-2-quinolinyl}-1,3-indandione,

(26) 4,5,6,7-tetrachloro(or tetrabromo)-2-{8-bromo-5(or 6)-[5,8-dibromonaphthalene-2,3-dicarboximido]-2-quinolinyl}-1,3-indandione,

(27) 4,5,6,7-tetrachloro(or tetrabromo)-2-{8-methyl-5(or 6)-[5,8-dibromonaphthalene-2,3-dicarboximido]-2-quinolinyl}-1,3-indandione, (28) 4,5,6,7-tetrachloro(or tetrabromo)-2-{8-ethyl-5(or 6)-[5,8-dibromonaphthalene-2,3-dicarboximido]-2-quinolinyl}-1,3-indandione,

(29) 4,5,6,7-tetrachloro(or tetrabromo)-2-{8-methoxy-5(or 6)-[5,8-dibromonaphthalene-2,3-dicarboximido]-2-quinolinyl}-1,3-indandione,

(30) 4,5,6,7-tetrachloro(or tetrabromo)-2-{8-ethoxy-5(or 6)-[5,8-dibromonaphthalene-2,3-dicarboximido]-2-quinolinyl}-1,3-indandione,

(31) 4,5,6,7-tetrachloro(or tetrabromo)-2-{8-chloro-5(or 6)-[5,6,7,8-tetrabromonaphthalene-2,3-dicarboximido-]-2-quinolinyl}-1,3-indandione,

(32) 4,5,6,7-tetrachloro(or tetrabromo)-2-{8-bromo-5(or 6)-[5,6,7,8-tetrabromonaphthalene-2,3-dicarboximido-]-2-quinolinyl}-1,3-indandione,

(33) 4,5,6,7-tetrachloro(or tetrabromo)-2-{8-methyl-5(or 6)-[5,6,7,8-tetrabromonaphthalene-2,3-dicarboximido-]-2-quinolinyl}-1,3-indandione,

(34) 4,5,6,7-tetrachloro(or tetrabromo)-2-{8-ethyl-5(or 6)-[5,6,7,8-tetrabromonaphthalene-2,3-dicarboximido-]-2-quinolinyl]-1,3-indandione,

(35) 4,5,6,7-tetrachloro(or tetrabromo)-2-{8-methoxy-5(or 6)-[5,6,7,8-tetrabromonaphthalene-2,3-dicarboximido]-2-quinolinyl}-1,3-indandione,

(36) 4,5,6,7-tetrachloro(or tetrabromo)-2-{8-ethoxy-5(or 6)-[5,6,7,8-tetrabromonaphthalene-2,3-dicarboximido]-2-quinolinyl}-1,3-indandione,

(37) 4,5,6,7-tetrachloro(or tetrabromo)-2-[8-chloro-5(or 6)-naphthalene-1,2-dicarboximido-2-quinolinyl]-1,3-indandione,

(38) 4,5,6,7-tetrachloro(or tetrabromo)-2-[8-bromo-5(or 6)-naphthalene-1,2-dicarboximido-2-quinolinyl]-1,3-indandione,

(39) 4,5,6,7-tetrachloro(or tetrabromo)-2-[8-methyl-5(or 6)-naphthalene-1,2-dicarboximido-2-quinolinyl]-1,3-indandione,

(40) 4,5,6,7-tetrachloro(or tetrabromo)-2-[8-ethyl-5(or 6)-naphthalene-1,2-dicarboximido-2-quinolinyl]-1,3-indandione,

(41) 4,5,6,7-tetrachloro(or tetrabromo)-2-[8-methoxy-5(or 6)-naphthalene-1,2-dicarboximido-2-quinolinyl]-1,3-indandione,

(42) 4,5,6,7-tetrachloro(or tetrabromo)-2-[8-ethoxy-5(or 6)-naphthalene-1,2-dicarboximido-2-quinolinyl]-1,3-indandione,

(43) 4,5,6,7-tetrachloro(or tetrabromo)-2-[8-chloro-5(or 6)-benzenesulfonylnaphthalene-2,3-dicarboximido-2-quinolinyl]-1,3-indandione,

(44) 4,5,6,7-tetrachloro(or tetrabromo)-2-[8-bromo-5(or 6)-benzenesulfonylnaphthalene-2,3-dicarboximido-2-quinolinyl]-1,3-indandione,
(45) 4,5,6,7-tetrachloro(or tetrabromo)-2-[8-methyl-5(or 6)-benzenesulfonylnaphthalene-2,3-dicarboximido-2-quinolinyl]-1,3-indandione,
(46) 4,5,6,7-tetrachloro(or tetrabromo)-2-[8-ethyl-5(or 6)-benzenesulfonylnaphthalene-2,3-dicarboximido-2-quinolinyl]-1,3-indandione,
(47) 4,5,6,7-tetrachloro(or tetrabromo)-2-[8-methoxy-5(or 6)-benzenesulfonylnaphthalene-2,3-dicarboximido-2-quinolinyl]-1,3-indandione,
(48) 4,5,6,7-tetrachloro(or tetrabromo)-2-[8-ethoxy-5(or 6)-benzenesulfonylnaphthalene-2,3-dicarboximido-2-quniolinyl]-1,3-indandione,
(49) 4,5,6,7-tetrachloro(or tetrabromo)-2-[8-chloro-5(or 6)-diphenimido-2-quinolinyl]-1,3-indandione,
(50) 4,5,6,7-tetrachloro(or tetrabromo)-2-[8-bromo-5(or 6)-diphenimido-2-quinolinyl)-1,3-indandione,
(51) 4,5,6,7-tetrachloro(or tetrabromo)-2-[8-methyl-5(or 6)-diphenimido-2-quinolinyl]-1,3-indandione,
(52) 4,5,6,7-tetrachloro(or tetrabromo)-2-[8-ethyl-5(or 6)-diphenimido-2-quinolinyl]-1,3-indandione,
(53) 4,5,6,7-tetrachloro(or tetrabromo)-2-[8-methoxy-5(or 6)-diphenimido-2-quinolinyl]-1,3-indandione,
(54) 4,5,6,7-tetrachloro(or tetrabromo)-2-[8-ethoxy-5(or 6)-diphenimido-2-quinolinyl]-1,3-indandione,
(55) 4,5,6,7-tetrachloro(or tetrabromo)-2-[8-chloro-5(or 6)-tetrachloro(or tetrabromo)phthalimido-4-methyl(or ethyl)-2-quinolinyl)-1,3-indandione,
(56) 4,5,6,7-tetrachloro(or tetrabromo)-2-[8-bromo-5(or 6)-tetrachloro(or tetrabromo)phthalimido-4-methyl(or ethyl)-2-quinolinyl]-1,3-indandione,
(57) 4,5,6,7-tetrachloro(or tetrabromo)-2-[8-methoxy-5(or 6)-tetrachloro(or tetrabromo)phthalimido-4-methyl(or ethyl)-2-quinolinyl]-1,3-indandione,
(58) 4,5,6,7-tetrachloro(or tetrabromo)-2-[8-ethoxy-5(or 6)-tetrachloro(or tetrabromo)phthalimido-4-methyl(or ethyl)-2-quinolinyl]-1,3-indandione,
(59) 4,5,6,7-tetrachloro(or tetrabromo)-2-[8-chloro-5(or 6)-tetrachloro(or tetrabromo)phthalimido-3,4-dimethyl-2-quinolinyl]-1,3-indandione,
(60) 4,5,6,7-tetrachloro(or tetrabromo)-2-[8-bromo-5(or 6)-tetrachloro(or tetrabromo)phthalimido-3,4-dimethyl-2-quinolinyl]-1,3-indandione,
(61) 4,5,6,7-tetrachloro(or tetrabromo)-2-[8-ethyl-5(or 6)-tetrachloro(or tetrabromo)phthalimido-3,4-dimethyl-2-quinolinyl]-1,3-indandione,
(62) 4,5,6,7-tetrachloro(or tetrabromo)-2-[8-methoxy-5(or 6)-tetrachloro(or tetrabromo)phthalimido-3,4-dimethyl-2-quinolinyl]-1,3-indandione,
(63) 4,5,6,7-tetrachloro(or tetrabromo)-2-[8-ethoxy-5(or 6)-tetrachloro(or tetrabromo)phthalimido-3,4-dimethyl-2-quinolinyl]-1,3-indandione,
(64) 4,5,6,7-tetrachloro(or tetrabromo)-2-[3,4,8-trimethyl-5(or 6)-tetrachloro(or tetrabromo)phthalimido-2-quinolinyl]-1,3-indandione,
(65) 4,5,6,7-tetrachloro(or tetrabromo)-2-[5(or 6)tetrachloro(or tetrabromo)phthalimido-2-quinolinyl]-1,3-indandione,
(66) 4,5,6,7-tetrachloro(or tetrabromo)-2-[6-chloro-5-tetrachloro(or tetrabromo)phthalimido-2-quinolinyl]-1,3-indandione,
(67) 4,5,6,7-tetrachloro(or tetrabromo)-2-[6-methyl-5-tetrachloro(or tetrabromo)phthalimido-2-quinolinyl]-1,3-indandione,
(68) 4,5,6,7-tetrachloro(or tetrabromo)-2-[5(or 6)tetrachloro(or tetrabromo)phthalimido-4,8-dimethyl-2-quinolinyl]-1,3-indandione.

The compound of formula (I) can be easily produced, for example, by reacting a quinaldine derivative of the formula

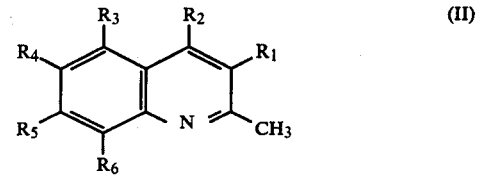

wherein $R_1$, $R_2$, $R_3$, $R_4$, $R_5$ and $R_6$ are the same as defined hereinabove, with a tetrahalophthalic acid of the formula

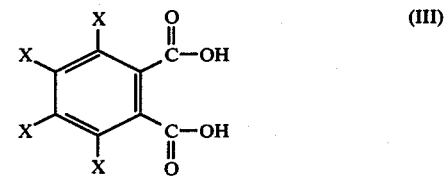

wherein X is the same as defined hereinabove, or its reactive derivative.

The reaction between the quinaldine derivative of formula (II) and the tetrahalophthalic acid of formula (III) or its reactive derivative may be carried out in the absence of solvent. Generally, however, it is performed in the presence of a solvent. Useful solvents are organic solvents which are inert under the reaction conditions, for example, hydrocarbons such as decalin, tetralin or trimethylbenzene; halogenated hydrocarbons such as dichlorobenzene, trichlorobenzene or chloronaphthalene, nitrated hydrocarbons such as nitrobenzene; ethers as diphenyl ether; and N-methylpyrrolidone.

The reaction is carried out generally under heat. The heating temperature can be varied over a wide range according, for example, to the types and proportions of the starting materials, or the type of the solvent. Usually, it is 100° to 300° C., preferably 150° to 270° C. The reaction pressure is usually normal atmospheric pressure, but if desired, the reaction may be performed at a reduced or elevated pressure. Within the above temperature range, the reaction ends generally in 2 to 10 hours.

The proportions of the quinaldine derivative of formula (II) and the tetrahalophthalic acid of formula (III) or its reactive derivative are not critical, and can be varied over a wide range according, for example, to the starting materials or the reaction conditions. It is generally advantageous that the tetrahalophthalic acid or its reactive derivative is used in an amount at least eqimolar to the quinaldine derivative, preferably in a somewhat excessive amount (1.2 to 3 molar times, especially about 2.0 molar times).

The reaction sufficiently proceeds by heating the two starting materials under the above reaction conditions. Advantageously, however, the reaction can be carried out in the presence of a catalytic amount of a Friedel-Crafts catalyst, such as zinc chloride, aluminium chloride, antimony pentoxide, iron trichloride, tin tetrachloride, or titanium tetrachloride. The presence of the catalyst is especially necessary when the reaction temperature is relatively low, for example, not more than about 250° C. because at such temperatures, the rate of the reaction decreases.

Water formed as a by-product in the above reaction should desirably be removed out of the reaction system during the reaction by a suitable means such as evaporation, use of a dehydrating agent, or azeotropic distillation.

Typical examples of the quinaldine derivative of formula (II) used as a starting material in the above reaction are:

5(or 6)-phthalimido-8-chloro-quinaldine,
5(or 6)-phthalimido-8-bromo-quinaldine,
5(or 6)-phthalimido-8-methyl-quinaldine,
5(or 6)-phthalimido-8-ethyl-quinaldine,
5(or 6)-phthalimido-8-methoxy-quinaldine,
5(or 6)-phthalimido-8-ethoxy-quinaldine,
5(or 6)-tetrachloro(or tetrabromo)phthalimido-8-chloro-quinaldine,
5(or 6)-tetrachloro(or tetrabromo)phthalimido-8-bromo-quinaldine,
5(or 6)-tetrachloro(or tetrabromo)phthalimido-8-methyl-quinaldine,
5(or 6)-tetrachloro(or tetrabromo)phthalimido-8-ethyl-quinaldine,
5(or 6)-tetrachloro(or tetrabromo)phthalimido-8-methoxy-quinaldine,
5(or 6)-tetrachloro(or tetrabromo)phthalimido-8-ethoxy-quinaldine,
5(or 6)-naphthalimido-8-chloro-quinaldine,
5(or 6)-naphthalimido-8-bromo-quinaldine,
5(or 6)-naphthalimido-8-methyl-quinaldine,
5(or 6)-naphthalimido-8-ethyl-quinaldine,
5(or 6)-naphthalimido-8-methoxy-quinaldine,
5(or 6)-naphthalimido-8-ethoxy-quinaldine,
5(or 6)-[3(or 4)-chloro(or bromo)-naphthalimido]-8-chloro-quinaldine,
5(or 6)-[3(or 4)-chloro(or bromo)-naphthalimido]-8-bromo-quinaldine,
5(or 6)-[3(or 4)-chloro(or bromo)-naphthalimido]-8-methyl-quinaldine,
5(or 6)-[3(or 4)-chloro(or bromo)-naphthalimido]-8-ethyl-quinaldine,
5(or 6)-[3(or 4)-chloro(or bromo)-naphthalimido]-8-methoxy-quinaldine,
5(or 6)-[3(or 4)-chloro(or bromo)-naphthalimido]-8-ethoxy-quinaldine,
5(or 6)-naphthalene-2,3-dicarboximido-8-chloro-quinaldine,
5(or 6)-naphthalene-2,3-dicarboximido-8-bromoquinaldine,
5(or 6)-naphthalene-2,3-dicarboximido-8-methylquinaldine,
5(or 6)-naphthalene-2,3-dicarboximido-8-ethylquinaldine,
5(or 6)-naphthalene-2,3-dicarboximido-8-methoxyquinaldine,
5(or 6)-naphthalene-2,3-dicarboximido-8-ethoxyquinaldine,
5(or 6)-(5,8-dibromo-naphthalene-2,3-dicarboximido)-8-chloro-quinaldine,
5(or 6)-(5,8-dibromo-naphthalene-2,3-dicarboximido)-8-bromo-quinaldine,
5(or 6)-(5,8-dibromo-naphthalene-2,3-dicarboximido)-8-methyl-quinaldine,
5(or 6)-(5,8-dibromo-naphthalene-2,3-dicarboximido)-8-ethyl-quinaldine,
5(or 6)-(5,8-dibromo-naphthalene-2,3-dicarboximido)-8-methoxy-quinaldine,
5(or 6)-(5,8-dibromo-naphthalene-2,3-dicarboximido)-8-ethoxy-quinaldine,
5(or 6)-(5,6,7,8-tetrabromo-naphthalene-2,3-dicarboximido)-8-chloro-quinaldine,
5(or 6)-(5,6,7,8-tetrabromo-naphthalene-2,3-dicarboximido)-8-bromo-quinaldine,
5(or 6)-(5,6,7,8-tetrabromo-naphthalene-2,3-dicarboximido)-8-methyl-quinaldine,
5(or 6)-(5,6,7,8-tetrabromo-naphthalene-2,3-dicarboximido)-8-ethyl-quinaldine,
5(or 6)-(5,6,7,8-tetrabromo-naphthalene-2,3-dicarboximido)-8-methoxy-quinaldine,
5(or 6)-(5,6,7,8-tetrabromo-naphthalene-2,3-dicarboximido)-8-ethoxy-quinaldine,
5(or 6)-(naphthalene-1,2-dicarboximido)-8-chloro-quinaldine,
5(or 6)-(naphthalene-1,2-dicarboximido)-8-bromo-quinaldine,
5(or 6)-(naphthalene-1,2-dicarboximido)-8-methyl-quinaldine,
5(or 6)-(naphthalene-1,2-dicarboximido)-8-ethyl-quinaldine,
5(or 6)-(naphthalene-1,2-dicarboximido)-8-methoxy-quinaldine,
5(or 6)-(naphthalene-1,2-dicarboximido)-8-ethoxy-quinaldine,
5(or 6)-diphenimido-8-chloro-quinaldine,
5-(or 6)-diphenimido-8-bromo-quinaldine,
5(or 6)-diphenimido-8-methyl-quinaldine,
5(or 6)-diphenimido-8-ethyl-quinaldine,
5(or 6)-diphenimido-8-methoxy-quinaldine,
5(or 6)-diphenimido-8-ethoxy-quinaldine,
5(or 6)-tetrachloro(or tetrabromo)phthalimido-8-chloro-4-methyl(or ethyl)-quinaldine,
5(or 6)-tetrachloro(or tetrabromo)phthalimido-8-bromo-4-methyl(or ethyl)-quinaldine,
5(or 6)-tetrachloro(or tetrabromo)phthalimido-8-methyl-4-methyl(or ethyl)-quinaldine,
5(or 6)-tetrachloro(or tetrabromo)phthalimido-8-ethyl-4-methyl(or ethyl)-quinaldine,
5(or 6)-tetrachloro(or tetrabromo)phthalimido-8-methoxy-4-methyl(or ethyl)-quinaldine,
5(or 6)-tetrachloro(or tetrabromo)phthalimido-8-ethoxy-4-methyl(or ethyl)-quinaldine,
5(or 6)-tetrabromo(or tetrachloro)phthalimido-8-chloro-3,4-dimethyl-quinaldine,
5(or 6)-tetrabromo(or tetrachloro)phthalimido-8-bromo-3,4-dimethyl-quinaldine,
5(or 6)-tetrabromo(or tetrachloro)phthalimido-8-methyl-3,4-dimethyl-quinaldine,
5(or 6)-tetrabromo(or tetrachloro)phthalimido-8-ethyl-3,4-dimethyl-quinaldine,
5(or 6)-tetrabromo(or tetrachloro)phthalimido-8-methoxy-3,4-dimethyl-quinaldine,
5(or 6)-tetrabromo(or tetrachloro)phthalimido-8-ethoxy-3,4-dimethyl-quinaldine, and
5(or 6)-tetrabromo(or tetrachloro)phthalimido-quinaldine-6-chloro(or methyl)-5-tetrachloro(or tetrabromo)phthalimido-quinaldine.

The tetrahalophthalic acids of formula (III) are known, and for example, tetrachlorophthalic acid and tetrabromophthalic acid can be suitably used. The reactive derivatives of the tetrahalophthalic acids are, for example, their anhydrides and esters, especially lower alkyl esters.

The quinaldine derivative of formula (II) used as a starting material is a novel compound, and can be prepared, for example, by reacting a 5- or 6-aminoquinaldine derivative of the formula

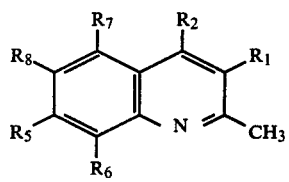

wherein one of $R_7$ and $R_8$ represents an amino group, and the other represents a hydrogen atom, a halogen atom or a lower alkyl group; and $R_1$, $R_2$, $R_5$ and $R_6$ are the same as defined hereinabove; with the proviso that when $R_7$ represents an amino group, $R_2$ represents a hydrogen or halogen atom, with an aryldicarboxylic acid of the following formula

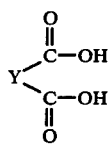

wherein Y is the same as defined hereinabove, or its reactive derivative.

The reaction between the compound of formula (IV) and the compound of formula (V) can be performed by heating them in the absence of a solvent, or preferably in the presence of a solvent of the type described hereinabove. Generally, this reaction is carried out under milder reaction conditions than the reaction conditions used to react the quinaldine derivative of formula (II) with the tetrahalophthalic acid of formula (III) or its reactive derivative. For example, the heating temperature is generally 100° to about 250° C. But when the reaction temperature increases, not only will the amino group at the 5- or 6-position of the compound of formula (IV) be condensed with the compound of formul (V), but also there will be an increasing tendency for the methyl group at the 2-position to be attacked by the compound of formula (V) or its reactive derivative. When such a high reaction temperature is used, appropriate measures, for example, the shortening of the reaction time, are taken to produce the compound of formula (II) predominantly. This reaction does not require catalysts.

The ratio between the compound of formula (IV) and the compound of formula (V) or its reactive derivative is not critical, but advantageously, the molar ratio of the former to the latter is adjusted to about 1:1 to about 1:1.2.

The compound of formula (II) so prepared may be used in the reaction of forming the quinoline derivative in accordance with this invention, either directly without isolation, or after isolation. When it is not isolated, it is desirable that the compound of formula (IV) and the compound of formula (V) or its reactive derivative be reacted in substantially equimolar ratios.

According to another aspect of this invention, a compound of formula (I) in which Y represents the group of the formula

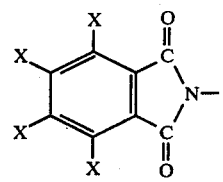

can be produced directly from the 5- or 6-aminoquinaldine derivative of formula (IV) by reacting it with the tetrahalophthalic acid of formula (III) or its reactive derivative. This reaction can be performed under the same conditions as described hereinabove with regard to the reaction of the quinaldine derivative of formula (II) with the tetrahalophthalic acid of formula (III) or its reactive derivative. The ratio between the 5- or 6-aminoquinaldine derivative of formula (IV) and the tetrahalophthalic acid of formula (III) or its reactive derivative is not critical, and advantageously, at least 2 moles (preferably up to about 6 moles) of the tetrahalophthalic acid of formula (III) is used per mole of the compound of formula (IV).

Typical examples of the 5- or 6-aminquinaldine derivatives of formula (IV) used as a starting material in the above reaction include:
  5(or 6)-amino-8-chloro-quinaldine,
  5(or 6)-amino-8-bromo-quinaldine,
  5(or 6)-amino-8-methyl-quinaldine,
  5-(or 6)-amino-8-ethyl-quinaldine,
  5(or 6)-amino-8-methoxy-quinaldine,
  5-(or 6)-amino-8-ethoxy-quinaldine,
  5(or 6)-amino-8-chloro-4-methyl(or ethyl)-quinaldine,
  5(or 6)-amino-8-bromo-4-methyl(or ethyl)-quinaldine,
  5(or 6)-amino-8-methoxy-4-methyl(or ethyl)-quinaldine,
  5(or 6)-amino-8-ethoxy-4-methyl(or ethyl)-quinaldine,
  5-(or 6)-amino-4,8-dimethyl(or diethyl)-quinaldine,
  5(or 6)-amino-4-ethyl-8-methyl(or ethyl)-quinaldine,
  5(or 6)-amino-3,4,8-trimethyl-quinaldine,
  5-(or 6)-amino-quinaldine,
  5(or 6)-amino-3,4-dimethyl-quinaldine,
  5(or 6)-amino-4-methyl(or ethyl)quinaldine.

Examples of the aryldicarboxylic acid of formula (V) to be reacted with the 5- or 6-aminoquinaldine derivative of formula (IV) include:
  phthalic acid,
  monochloro(or monobromo)phthalic acid,
  dichloro(or dibromo)phthalic acid,
  tetrachloro(or tetrabromo)phthalic acid,
  naphthalic acid,
  3(or 4)-chloronaphthalic acid,
  3(or 4)-bromonaphthalic acid,
  naphthalene-2,3-dicarboxylic acid,
  5,8-dibromo-naphthalene-2,3-dicarboxylic acid,
  5,6,7,8-tetrabromo-naphthalene-2,3-dicarboxylic acid,
  naphthalene-1,2-dicarboxylic acid,
  benzenesulfonyl-naphthalene-2,3-dicarboxylic acid,
  hexachloro(or hexabromo)-naphthalic acid,
  dichloro(or dibromo)naphthalene-1,2-dicarboxylic acid, and
  6',7',-phthaloyl-phthalic acid.

Advantageously, the reactive derivatives of these aryldicarboxylic acids include anhydrides or esters, especially lower alkyl esters.

Some of the 5- or 6-aminoquinaldine derivatives of formula (IV) are also novel compounds, and can be prepared, for example, through the following steps.

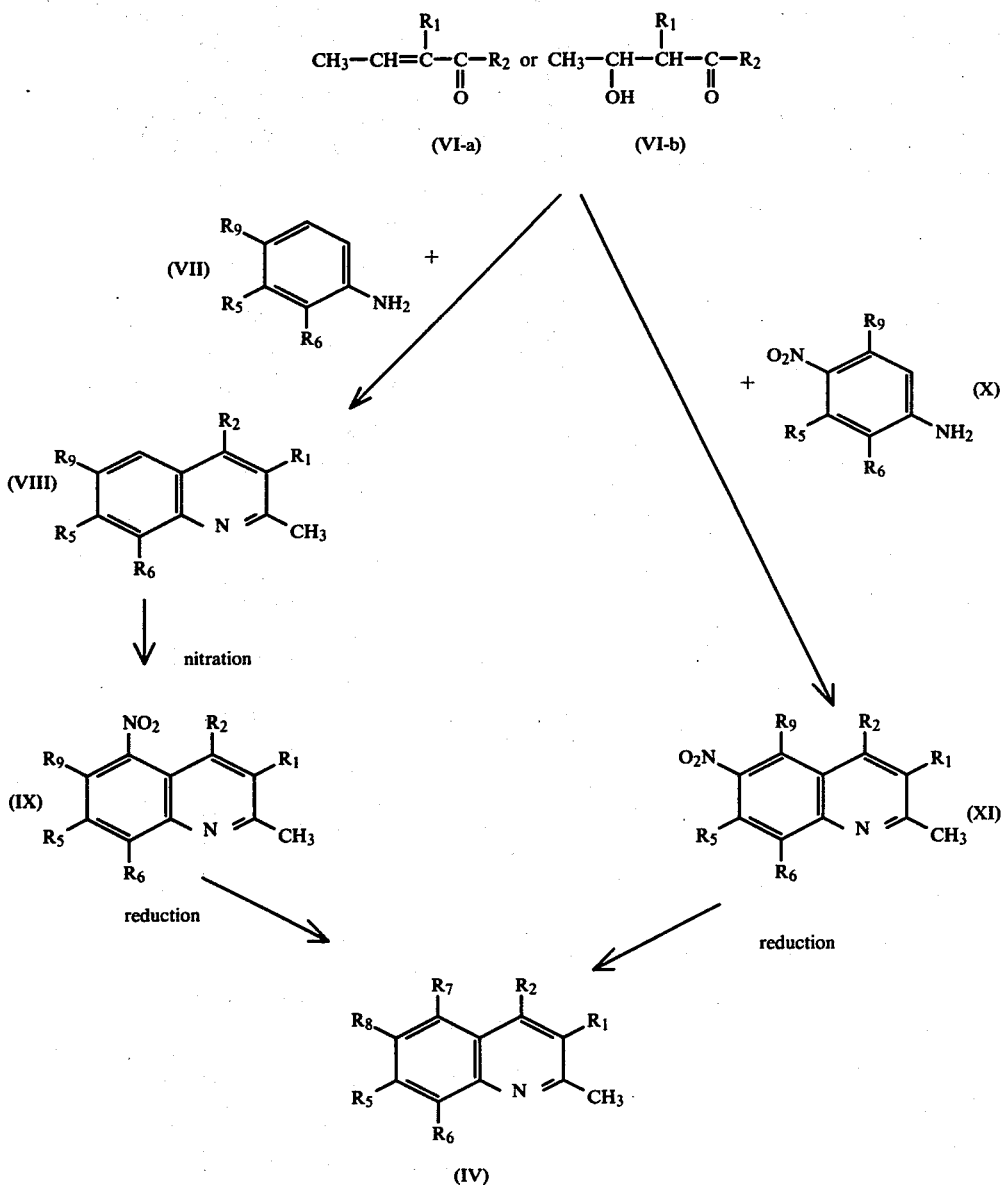

wherein $R_9$ represents a hydrogen atom, a halogen atom or a lower alkyl group; and $R_1$, $R_2$, $R_5$, $R_6$, $R_7$ and $R_8$ are the same as defined hereinabove.

The reaction of the compound of formula (VI-a) or (VI-b) with the compound of formula (VII) or (X) can be carried out by the "Doebner-Miller synthesis" method or its modified version [see, for example, Robert C. Elderfield, Heterocyclic Compounds, Vol. IV, Chap. I., pages, 1 to 344 (1952), published by John Wiley & Sons, Inc.]. Nitration of the compound of formula (VIII) and reduction of the compound of formula (IX) or (XI) can be carried out by ordinary methods.

The product of formula (I) can be separated from the reaction mixture and purified by any known method. For example, the reaction mixture after the reaction is cooled, and the resulting precipitated is separated and recovered by, for example, filtration or centrifugal separation. The compound of formula (I) so recovered has a sufficiently high purity, and can be used in applications to be described below. It may, if desired, be further purified by washing once or several times with an organic solvent, for example, alcohols such as methanol or ethanol, ketones such as acetone or methyl ethyl ketone, amides such as dimethylformamide or dimethylacetamide, N-methylpyrrolidone, or α-chloronaphthalene. An alternative procedue comprises first adding the organic solvent to the reaction mixture, cooling the mixture and separating and recovering the compound of formula (I) precipitated. If desired, the product of formula (I) recovered may be washed further with the organic solvent.

The compound of formula (I) can be subjected to a pigment-forming treatment by a method known in the art of pigment chemistry. For example, the compound is dissolved in conc. sulfuric acid, and the solution is poured into water to re-precipitate the compound in the form of a fine powder. Or the compound is finely pulverized by a pulverizer such as a ball mill.

The compounds of formula (I) provided by the present invention have yellow colors, and superior thermal stability, weatherability, solvent resistance and migration resistance. While the compounds of the formula given hereinabove which are disclosed in U.S. Pat. No. 3,622,583 cited hereinabove have a tendency to discoloration upon contact with frequently used additives for resins such as zinc stearate, the compounds of formula (I) are completely free from this disadvantage. These superior properties enable the compounds to be advantageously used as a coloring component of yellow organic pigments.

The compounds of formula (I) are useful as yellow organic pigments, and just the same as ordinary organic pigments, can be used in a wide range of applications, for example, for coloring polymeric shaped articles, or as coloring components of paints, printing inks, crayon, painting pastes and textile printing pastes.

In particular, the compounds of formula (I) can be advantageously used for coloring a variety of polymeric materials such as polyolefins, polystyrene, acrylic resins, vinyl resins, polyamides, polyesters, acetal resins, polycarbonates, ABS resins, amino resins, regenerated cellulose, epoxy resins, phenolic resins, urea resins, melamine resins, and polyimides.

In the present specification and the appended claims, the term "polymeric material" is meant to include not only shaped articles prepared from the above resins, but also compositions containing these resins as a binder, carrier, or vehicle, etc., for example, paints, printing inks and textile printing pastes.

One procedure available for coloring a shaped article of a resin using the compound of formula (I) comprises incorporating the compound of formula (I) in a desired amount (for example, 0.05 to 1 part by weight, preferably 0.1 to 0.5 part by weight, per 100 parts by weight of the resin) in the resin, melting or melt-kneading the resulting blend, and fabricating it into a desired shape such as a film, sheet, plate, pipe, tube, filament, or pellet by a conventional resin fabricating method such as compression molding, injection molding, calendering or extrusion. According to another method, the compound of formula (I) is added in advance to monomers or prepolymers for forming the resin, and the mixture is polymerized and fabricated to form a colored shaped article of the resin in the above-mentioned form (the cast shaping method).

The compounds of formula (I) can also be used to color fibers, woven or knitted fabrics, and nonwoven fabrics. They can be applied by a dip dyeing method same as in the case of disperse dyes, or by a textile printing technique.

Coloration can also be performed by adding the compound of formula (I) as a coloring agent to paints, lacquers, baking paints, powder paints, and aqueous emulsion paints, etc. It can also be used as a coloring agent for printing inks by adding it together with polymeric materials used for printing inks.

The following Examples and Comparative Examples illustrate the present invention in greater detail.

EXAMPLE 1

(A) A mixture consisting of 128 g (1.0 mole) of o-chloroaniline, 304 g of conc. hydrochloric acid and 61 g of water was maintained at 90°–95° C., and with sufficient stirring, 70 g (1.0 mole) of crotonaldehyde was added dropwise over the course of 2 hours. After the addition, the mixture was reacted further at 90°–95° C. for 1 hour. The reaction mixture was cooled, and then rendered alkaline by adding a conc. aqueous solution containing 132 g of sodium hydroxide with ice cooling. The alkaline mixture was separated into layers, and the oily layer was distilled at 2–3 mmHg to afford 72 g (0.4 mole) of 8-chloroquinaldine.

(B) 53.3 g (0.3 mole) of the resulting 8-chloroquinaldine was dissolved in 180.2 g of 98% sulfuric acid, and at 40° C., 40.2 g of nitric acid (specific gravity 1.50) was added dropwise over the course of 1 hour, followed by further reaction for 30 minutes. The reaction mixture was poured into ice water, and neutralized with an aqueous solution of sodium hydroxide. The product precipitated was collected by filtration, washed with water, and dried to afford 64.1 g (0.29 mole) of 8-chloro-5-nitroquinaldine.

(C) 85 g of iron powder was dispersed in a mixture consisting of 130 g of ethanol, 30 g of water, and 3 g of 35% hydrochloric acid. The dispersion was heated to 80°–90° C., and 44.0 g (0.25 mole) of 5-nitro-8-chloroquinaldine obtained by the procedure set forth in section (B) above was added. The mixture was stirred for 1 hour. After the reaction, the reaction mixture was neutralized with an aqueous solution of sodium carbonate, and the iron powder was separated by filtration. The iron powder was washed with 200 g of hot ethanol. The wash liquid and the filtrate were combined, and ethanol was evaporated off. The crystals precipitated were separated by filtration, washed with water, and dried to afford 43.3 g (0,22 mole) of 8-chloro-5-amino-quinaldine.

(D) 95 g of trichlorobenzene was added to 23.3 g (0.12 mole) of 8-chloro-5-amino-quinaldine and 18.0 g (0.12 mole) of phthalic anhydride, and the mixture was reacted under reflux for 2 hours at the boiling point. After cooling, the precipitated crystals were separated by filtration, and dried to afford 32 g (0.10 mole) of 8-chloro-5-phthalimidoquinaldine.

(E) 43 g (0.15 mole) of 3,4,5,6-tetrachlorophthalic anhydride, 200 g of trichlorobenzene and 4 g of anhydrous zinc chloride were added to the product of paragraph (D) above, and the mixture was reacted under reflux for 3 hours. Then, 50 g of dimethylformamide was added, and the mixture stirred for 1 hour under reflux.

(F) The reaction mixture was then cooled, and filtered. The resulting yellow product was washed with 100 g of dimethylformamide and then with ethanol, and dried to afford 54.5 g (0.09 mole) of a yellow compound of the following structural formula (1). The maximum absorption wavelength of its visible spectrum was 427 m$\mu$ [determined in a dimethylformamide (DMF) solution]. The product had a melting point of more than 360° C., and an infrared spectroscopic analysis (KBr) of the product showed characteristic absorptions at 1793 cm$^{-1}$ and 1730 cm$^{-1}$ ascribable to the carbonyl in the imide linkage, and characteristic absorptions at 1693 cm$^{-1}$ and 1640 cm$^{-1}$ ascribable to the carbonyl of the indandione. From these data and the mass spectral data of the product, the resulting reaction product was determined to be 4,5,6,7-tetrachloro-2-(8-chloro-5-phthalimido-2-quinolinyl)-1,3-indandione of the formula:

(1)

[Structure of compound (1)]

EXAMPLES 2 TO 11

The procedure of paragraph (D) of Example 1 was repeated except that compounds of the following formulae (2-1) and (2-2) were used in the same molar ratios instead of the 8-chloro-5-aminoquinaldine and phthalic anhydride set forth in paragraph (D) of Example 1.

(2-1)

[Structure with $NH_2$, $R_{63}$, $CH_3$]

(2-2)

[Anhydride structure with $Y_3$]

wherein $R_{63}$ and $Y_3$ are shown in Table 1.

To the resulting imidized quinaldine derivative was added a compound of the formula (2-3)

[Structure with $X_4$ substituents]

(wherein $X_4$ is as defined in Table 1) in the same molar ratio as the tetrachlorophthalic anhydride set forth in paragraph (E) of Example 1. By repeating the same procedure as set forth in paragraphs (E) and (F) of Example 1, yellow compounds were obtained. The results of their infrared spectroscopic analysis and the absorption maximum wavelengths ($\lambda_{max}$) of their visible spectra were as shown in Table 1. Hence, the resulting compounds were determined to be compounds of the formula

[Structure with $Y_3$, $R_{63}$, $X_4$ substituents]

(wherein $X_4$, $Y_3$, and $R_{63}$ are as shown in Table 1).

Table 1

| Example | $R_{63}$ | $Y_3$ | $X_4$ | IR characteristic absorptions (KBr) [cm$^{-1}$] | $\lambda_{max}$ [m$\mu$] in DMF |
|---|---|---|---|---|---|
| 2 | Cl | 3,4,5,6-tetrachloro-1,2-phenylene | Cl | 1780, 1727, 1687, 1627 | 429 |
| 3 | " | 3,4,5,6-tetrabromo-1,2-phenylene | Br | 1783, 1727, 1687, 1627 | 431 |
| 4 | " | 3,4,5,6-tetrachloro-1,2-phenylene | " | 1780, 1730, 1687, 1627 | 435 |
| 5 | " | 3,4,5,6-tetrabromo-1,2-phenylene | Cl | 1780, 1737, 1693, 1633 | 442 |
| 6 | " | 4-bromo-1,8-naphthylene | " | 1706, 1673, 1627 | 426 |
| 7 | " | 5,6,7,8-tetrabromo-2,3-naphthylene | " | 1787, 1733, 1693, 1637 | 429 |
| 8 | " | 5,8-dibromo-2,3-naphthylene | " | 1780, 1733, 1686, 1633 | 429 |
| 9 | " | 2,3-naphthylene | " | 1790, 1723, 1693, 1633 | 427 |
| 10 | " | 1,8-naphthylene | " | 1700, 1673, 1627 | 425 |
| 11 | Br | 1,2-phenylene | " | 1790, 1735, 1695, 1635 | 427 |

EXAMPLE 12

172 g (1.0 mole) of 5-amino-8-methylquinaldine and 715 g (2.5 moles) of 3,4,5,6-tetrachlorophthalic anhydride were reacted in the presence of 40 g of anhydrous zinc chloride in 2,000 g of 1,2,4-trichlorobenzene under reflux at the boiling point for 3 hours. Then, 500 g of dimethylformamide was added, and the mixture was stirred for 1 hour under reflux at the boiling point.

The reaction mixture was filtered at 120° C. The yellow reaction product separated was washed with 1,000 g of dimethylformamide and then with ethanol, and dried to afford 597 g (0.84 mole) of a powdery yellow compound. It showed a maximum absorption at 420 m$\mu$ and 443 m$\mu$ in a visible absorption spectrum in a dimethylformamide solution. In its infrared spectrum, absorptions due to —CO—N—CO— were seen at 1725 cm$^{-1}$ and 1782 cm$^{-1}$, and absorptions due to —CO—C—CO—, at 1625 cm$^{-1}$ and 1685 cm$^{-1}$.

From the above data, the resulting product was determined to be a compound of the structural formula:

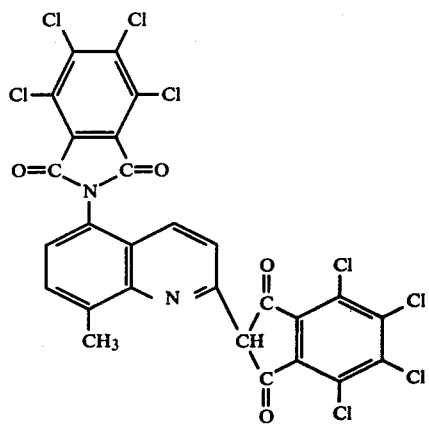

(3)

The elemental analysis values of the product for $C_{27}H_8O_4N_2Cl_8$ were as shown in Table 2.

Table 2

|  | C | H | N | Cl |
|---|---|---|---|---|
| Found (%) | 46.22 | 1.12 | 4.04 | 38.98 |
| Calculated (%) | 45.80 | 1.14 | 3.96 | 40.06 |

EXAMPLES 13 TO 15

Example 12 was repeated except that instead of 5-amino-8-methylquinaldine and tetrachlorophthalic anhydride, compounds of the formulae

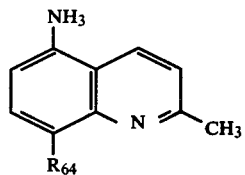

(4-1)

and

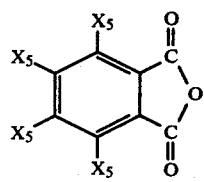

(4-2)

(wherein $R_{64}$ and $X_5$ are as shown in Table 3) were used in the same molar ratios as in Example 12 thereby to afford powdery yellow compounds. The infrared absorption spectra and the maximum wavelengths ($\lambda_{max}$) in their visible spectrum were as shown in Table 3. From these data, the resulting compounds were determined to be compounds of the structural formula

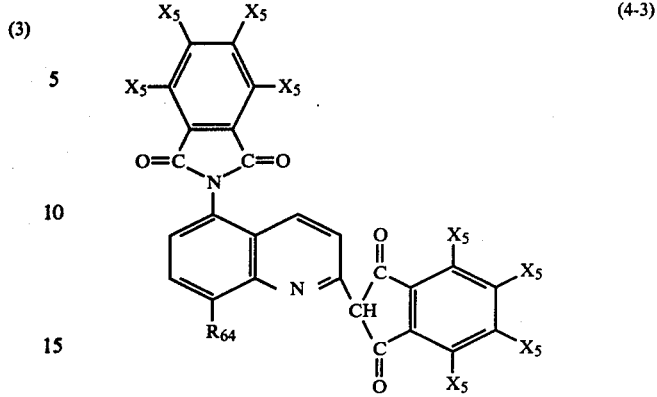

(4-3)

(wherein $R_{64}$ and $X_5$ are as shown in Table 3).

Table 3

| Example | $R_{64}$ | $X_5$ | IR characteristic absorptions (KBr) [cm$^{-1}$] | $\lambda_{max}$ [m$\mu$] in DMF |
|---|---|---|---|---|
| 13 | CH$_3$ | Br | 1778, 1732, 1690, 1630 | 422 |
| 14 | OCH$_3$ | Cl | 1775, 1730, 1690, 1635 | 422 |
| 15 | C$_2$H$_5$ | Cl | 1790, 1730, 1690, 1630 | 423 |

EXAMPLE 16

172 g (1.0 mole) of 5-amino-8-methylquinaldine and 464 g (1.0 mole) of 3,4,5,6-tetrabromophthalic anhydride were reacted in 2,000 g of trichlorobenzene for 2 hours under reflux to afford 532 g (0.86 mole) of 8-methyl-5-(3,4,5,6-tetrabromophthalimido)-quinaldine.

369 g (1.29 moles) of tetrachlorophthalic anhydride and 2,000 g of α-chloronaphthalene were added, and the mixture was reacted for 2 hours under reflux. The product was collected by hot filtration at 120° C., and dispersed in 1,000 g of α-chloronaphthalene, and the mixture was heated with stirring to wash the product. After hot filtration, the product was washed with ethanol and dried to afford 671 g (0.75 mole) of a yellow compound.

The maximum absorption wavelength of its visible absorption spectrum in a dimethylformamide solution was 421 m$\mu$, and in its infrared absorption spectrum (KBr), absorptions ascribable to —CO—N—CO— were observed at 1732 cm$^{-1}$ and 1780 cm$^{-1}$, and absorptions ascribable to —CO—C—CO—, at 1630 cm$^{-1}$ and 1690 cm$^{-1}$.

The elemental analysis values were as follows:

|  | C | H | N | halogen |
|---|---|---|---|---|
| Found (%) | 36.49 | 0.95 | 3.04 | 51.60 |
| Calculated (%) | 36.61 | 0.91 | 3.16 | 52.10 |

From the above data, this product was determined to be a compound of the structural formula:

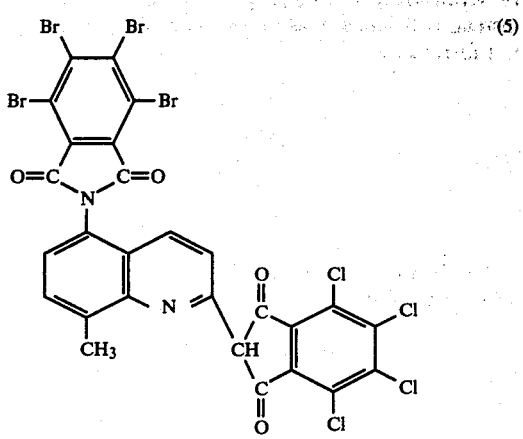
(5)

trum analysis of these compounds and the absorption maximum wavelength ($\lambda_{max}$) in their visible spectra were as shown in Table 4. From these data, the resulting compounds were determined to be compounds of the structural formula

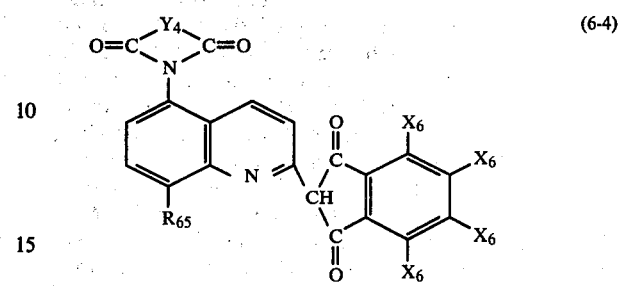
(6-4)

(wherein $R_{65}$, $Y_4$ and $X_6$ are as shown in Table 4).

Table 4

| Example | $R_{65}$ | $Y_4$ | $X_6$ | IR characteristic absorptions (KBr) [cm$^{-1}$] | $\lambda_{max}$ [mµ] in DMF |
|---|---|---|---|---|---|
| 17 | CH$_3$ | 1,2-phenylene | Cl | 1780, 1725, 1685, 1625 | 419 |
| 18 | OCH$_3$ | 1,8-naphthylene | " | 1715, 1700, 1685, 1630 | 421 |
| 19 | " | 1,2-naphthylene | " | 1780, 1730, 1690, 1635 | 421 |
| 20 | CH$_3$ | 2,3-naphthylene | " | 1780, 1725, 1680, 1630 | 420 |
| 21 | " | 5,8-dibromo-2,3-naphthylene | " | 1780, 1730, 1690, 1630 | 422 |
| 22 | " | 1,8-naphthylene | " | 1710, 1700, 1680, 1630 | 418 |
| 23 | " | 1,2-naphthylene | " | 1775, 1730, 1690, 1630 | 421 |
| 24 | " | tetrachloro-1,2-phenylene | Br | 1790, 1735, 1695, 1635 | 423 |
| 25 | OCH$_3$ | 1,2-phenylene | Cl | 1780, 1730, 1690, 1640 | 420 |

EXAMPLES 17 TO 25

Yellow compounds were prepared by repeating Example 16 except that a compound of the formula

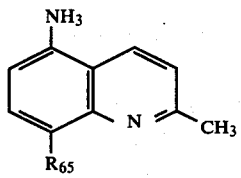
(6-1)

(wherein $R_{65}$ is as shown in Table 4) was used instead of 5-amino-8-methylquinaldine; a compound of the formula

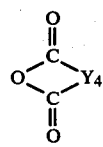
(6-2)

(wherein $Y_4$ is as shown in Table 4), instead of tetrabromophthalic anhydride; and a compound of the formula

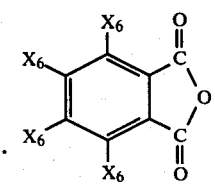
(6-3)

(wherein $X_6$ is as shown in Table 4), instead of tetrachlorophthalic anhydride, all in the same molar ratios as set forth in Example 16. The results of infrared spec-

EXAMPLE 26

(A) A mixture consisting of 608 g (4.0 moles) of 2-methyl-4-nitroaniline and 1,216 g of conc. hydrochloric acid was maintained at 90°-95° C., and with good stirring, 488 g (4.8 moles) of 2-pentanon-4-ol was added dropwise over a period of 2 hours. After the addition, the reaction was further carried out for 1 hour. After cooling, a conc. aqueous solution of 528 g of sodium hydroxide was added under ice cooling to render the reaction mixture alkaline. The alkaline reaction mixture was separated into layers, and the oily layer was distilled at 2-5 mmHg to afford 340 g (1.57 moles) of 6-nitro-4,8-dimethylquinaldine.

(B) 510 g of iron powder was dispersed in a mixture consisting of 780 g of ethanol, 180 g of water and 18 g of 35% hydrochloric acid, and the dispersion was heated to 80°-90° C. To the heated dispersion was added 262 g (1.21 moles) of 6-nitro-4,8-dimethylquinaldine obtained by the procedure of paragraph (A) above, and the mixture was stirred for 1 hour. After the reaction, an aqueous solution of sodium carbonate was added to neutralize the reaction mixture, and the iron powder was separated by filtration. The iron powder collected was washed with 1,200 g of hot ethanol. The wash liquid and the filtrate were combined, and ethanol was evaporated off. The crystals precipitated were separated by filtration, washed with water, and dried to afford 193 g (1.04 moles) of 6-amino-4,8-dimethylquinaldine.

(C) 350 g of o-dichlorobenzene was added to 186 g (1.0 mole) of 6-amino-4,8-dimethylquinaldine and 286 g (1.0 mole) of 3,4,5,6-tetrachlorophthalic anhydride, and the mixture was refluxed at the boiling point for 4 hours. The reaction mixture was then cooled. The crystals precipitated were collected by filtration, and dried to afford 394 g (0.87 mole) of 4,8-dimethyl-6-(3,4,5,6-tetrachlorophthalimido)-quinaldine. Then, 372 g (1.30 moles) of 3,4,5,6-tetrachlorophthalic anhydride, 2,000 g of 1,2,4-trichlorobenzene and 40 g of anhydrous zinc chloride were added, and the mixture was heated under reflux for 3 hours. Then, 500 g of dimethylformamide was added, and the mixture was stirred under reflux for 1 hour. The product was treated in the same way as in paragraph (C) of Example 1 to afford 571 g (0.79 mole) of a yellow compound. Since the compound obtained was scarcely soluble in dimethylformamide, its visible spectrum could not be measured. In its infrared spectrum (KBr), absorptions ascribable to —CO—N—CO— were observed at 1730 cm$^{-1}$ and 1790 cm$^{-1}$, and absorptions ascribable to —CO—C—CO—, at 1645 cm$^{-1}$ and 1695 cm$^{-1}$. The elemental analysis values of this product were as follows:

|  | C | H | N. | Cl |
|---|---|---|---|---|
| Found (%) | 47.21 | 1.40 | 3.92 | 38.50 |
| Calculated (%) | 46.58 | 1.39 | 3.88 | 39.29 |

From the above data, the resulting yellow product was determined to be 4,5,6,7-tetrachloro-2-[4,8-dimethyl-6-(3,4,5,6-tetrachlorophthalimido)-2-quinolinyl]-1,3-indandione of the formula:

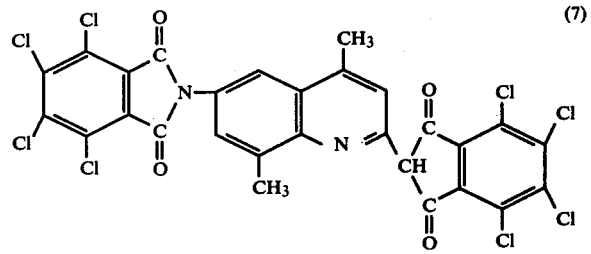
(7)

EXAMPLES 27 to 38

Yellow compounds were prepared by repeating Example 26 except that a compound of the formula:

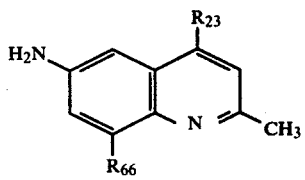
(8-1)

(wherein R$_{23}$ and R$_{66}$ are as shown in Table 5) was used instead of 6-amino-8-methylquinaldine; a compound of the formula

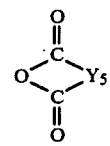
(8-2)

(wherein Y$_5$ is as shown in Table 5), instead of phthalic anhydride; and a compound of the formula

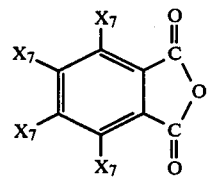
(8-3)

(wherein X$_7$ is as shown in Table 5), all in the same molar ratios as described in Example 26. The results of their infrared spectroscopic analysis and the absorption maximum wavelengths ($\lambda_{max}$) in their visible spectra were as shown in Table 5.

From these data, the resulting compounds were determined to be compounds of the formula

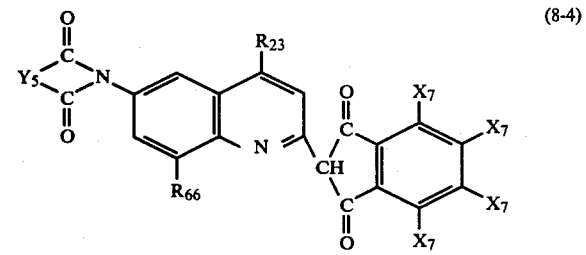
(8-4)

wherein R$_{66}$, R$_{23}$, Y$_5$ and X$_7$ are as shown in Table 5.

The asterisks in the column of $\lambda_{max}$ in Table 5 show that because the compounds were scarcely soluble in dimethylformamide, it was impossible to measure their visible spectral absorptions.

Table 5

| Example | R$_{66}$ | R$_{23}$ | Y$_5$ | X$_7$ | IR characteristic absorption (KBr) [cm$^{-1}$] | $\lambda_{max}$ [mμ] in DMF |
|---|---|---|---|---|---|---|
| 27 | Cl | H | 3,4,5,6-tetrachloro-1,2-phenylene | Cl | 1780, 1730, 1687, 1633 | * |
| 28 | CH$_3$ | " | " | " | 1790, 1734, 1690, 1640 | * |
| 29 | " | " | 1,2-phenylene | " | 1785, 1730, 1690, 1635 | 420 |
| 30 | " | CH$_3$ | " | " | 1780, 1730, 1695, 1640 | 420 |
| 31 | OCH$_3$ | H | 3,4,5,6-tetrachloro-1,2-phenylene | " | 1785, 1735, 1690, 1640 | 421 |
| 32 | Cl | CH$_3$ | " | " | 1778, 1730, 1688, 1635 | * |
| 33 | " | " | 1,2-phenylene | " | 1780, 1730, 1690, 1630 | 426 |
| 34 | " | " | 3,4,5,6-tetrabromo-1,2-phenylene | Br | 1765, 1728, 1682, 1638 | * |
| 35 | " | " | 3,4,5,6-tetrachloro-1,2-phenylene | " | 1779, 1732, 1686, 1640 | * |
| 36 | " | " | 3,4,5,6-tetrabromo-1,2-phenylene | Cl | 1770, 1737, 1687, 1640 | * |
| 37 | " | " | 1,8-naphthylene | " | 1720, 1712, 1680, 1630 | 428 |
| 38 | " | " | 2,3-naphthylene | " | 1770, 1720, 1690, 1631 | 430 |
| 39 | H | " | 3,4,5,6-tetrachloro-1,2-naphthylene | " | 1790, 1720, 1690, 1640 | * |

EXAMPLE 40

4,5,6,7-Tetrachloro-2-[8-chloro-5-(3,4,5,6-tetra-chlorophthalimido)-2-quinolinyl]-1,3-indandione of the structural formula

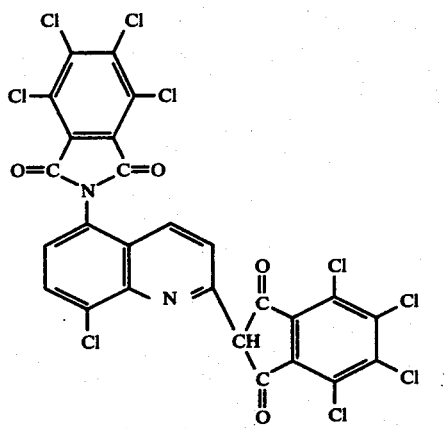

(9)

was tested for migration resistance, thermal stability and light stability by the following methods.

(A) Test for migration resistance

Two parts of the pigment, 300 parts of di(2-ethylhexyl)phthalate and 700 parts of polyvinyl chloride were mixed, and kneaded at 155° to 160° C. by two rolls. The resulting yellow sheet was held between white polyvinyl chloride sheets, and a pressure of 1 kg/cm² was applied to the assembly at 80° C. for 24 hours. The degree of migration resistance was evaluated by a gray scale.

(B) Test for thermal stability

The pigment (0.3 part) was mixed with 200 parts of polystyrene, and the mixture was extruded by a melt extruder at 230° C. to form pellets colored yellow. The pellets were injection-molded under the conditions shown in Table 6 to form molded plates. Differences in color according to the molding conditions were evaluated visually.

Table 6

| Injection-molding conditions | |
|---|---|
| Cylinder temperature (° C.) | Residence time (minutes) |
| 220 | 2 |
| 250 | 2 |
| 280 | 2 |

(C) Test for light stability

The injection-molded plates used in (B) above were examined for light stability by a Weather-Ometer (a product of Toyo Rika Instruments, Inc.) using a carbon-arc lamp, and the light stability was evaluated by a blue scale.

As a result of the above tests (A), (B) and (C), the compound of formula (9) had a migration resistance of grade 5 and a light stability of more than grade 6. In the thermal stability test, no difference in color was appreciable.

EXAMPLE 41

By the same method as set forth in paragraph (A) of Example 40, the pigment shown in Table 7 were tested for migration resistance. The numbers in the column of "pigment" correspond to those of Examples.

Table 7

| Run No. | Pigment | Migration resistance (grade) |
|---|---|---|
| 41-1 | 5 | 5 |
| 41-2 | 8 | 5 |
| 41-3 | 9 | 4 – 5 |
| 41-4 | 13 | 5 |
| 41-5 | 14 | 5 |
| 41-6 | 15 | 5 |
| 41-7 | 19 | 5 |
| 41-8 | 23 | 5 |
| 41-9 | 28 | 5 |
| 41-10 | 29 | 5 |
| 41-11 | 32 | 5 |
| 41-12 | 34 | 5 |
| 41-13 | 35 | 5 |
| 41-14 | 36 | 5 |

EXAMPLE 42

The pigments shown in Table 8 were tested for thermal stability and light stability by the same methods as set forth in paragraphs (B) and (C) of Example 40. The concentrations (parts per 200 parts of the resin) of the pigments are shown in Table 8, and the injection molding was performed under the conditions shown in Table 8 using each of the resins shown in Table 8. In the column of "injection-molding conditions", A denotes the conditions shown in Table 6, and B, the conditions shown in Table 9.

Table 8

| | Experimental conditions | | | | Evaluation | |
|---|---|---|---|---|---|---|
| Run No. | Pigment No. | Concentration of pigment | Resin | Injection molding conditions | Thermal stability | Light stability (grade) |
| 42-1 | 1 | 0.1 | Polyethylene with 0.5% TiO₂ | A | No difference | Above 6 |
| 42-2 | " | " | Polypropylene with 0.5% TiO₂ | " | " | " |
| 42-3 | " | 0.15 | Polycarbonate | B | " | " |
| 42-4 | 2 | " | " | " | " | " |
| 42-5 | 12 | " | " | " | " | " |
| 42-6 | 14 | 0.1 | Polystyrene | A | " | " |
| 42-7 | 34 | " | Polyethylene with 0.5% TiO₂ | " | " | 5 – 6 |
| 42-8 | 28 | 0.1 | Polystyrene | " | " | Above 6 |
| 42-9 | 31 | " | Polypropylene with 0.5% TiO₂ | A | " | 5 – 6 |
| 42-10 | 2 | " | ABS | " | Slightly changed | Above 6 |

Table 8-continued

| Run No. | Pigment No. | Concentration of pigment | Resin | Injection molding conditions | Thermal stability | Light stability (grade) |
|---|---|---|---|---|---|---|
| 42-11 | 2 | " | Polyester | B | No difference | " |
| 42-12 | 10 | " | Polyethylene with 0.5% TiO$_2$ | A | " | " |
| 42-13 | 17 | " | " | " | " | " |
| 42-14 | 9 | " | " | " | " | 5 – 6 |
| 42-15 | 8 | " | " | " | " | " |
| 42-16 | 38 | " | " | " | " | 5 |

Table 9

| Injection-molding conditions | |
|---|---|
| Cylinder temperature (° C.) | Residence time (minutes) |
| 300 | 2 |
| 300 | 10 |
| 300 | 20 |

COMPARATIVE EXAMPLE 1

The same tests as in Runs Nos. 42-1, 42-2 and 42-3 of Example 42 were performed using 4,5,6,7-tetrachloro-2-[8-(3,4,5,6-tetrachlorophthalimido)-2-quinolinyl]-1,3-indandione, a known pigment available under tradename PALIOTOL YELLOW 1090 (a product of BASF). It was found that the resulting injection-molded plates backened, and were quite useless.

EXAMPLE 43

An ester-interchange reactor equipped with a rectifying column and a methanol-distilling condenser was charged with 97 g of dimethyl terephthalate and 65 g of ethylene glycol, and 0.088 g of calcium acetate was added as a catalyst. The mixture was heated to 140° to 230° C. while distilling off methanol formed by the reaction. In about 3 hours, the temperature of the inside of the reactor reached 235° C., and a theoretical amount of methanol was distilled off, when 0.070 g of trimethyl phosphate was added to terminate the ester-interchange reaction.

Then, the reaction product was transferred to a polycondensation reactor equipped with a stirrer and an ethylene glycol distilling condenser. 0.044 g of antimony trioxide and 1.5 g of 4,5,6,7-tetrachloro-2-(8-chloro-5-phthalimido-2-quinolinyl-1,3-indandione of the following formula

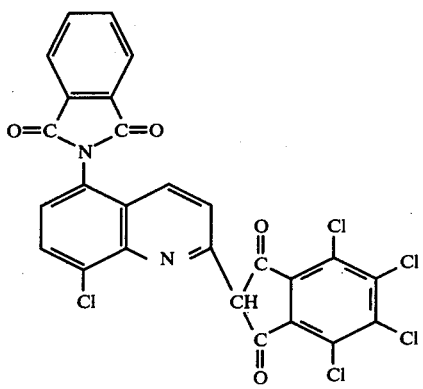

(10)

were added, and the polycondensation was carried out for 10 minutes at 280° C. under atmospheric pressure, for 30 minutes in a vacuum of 30 to 40 mmHg, and then for 1.5 hours in a high vacuum of 0.3 mmHg. The contents were cooled, withdrawn from the reactor, and pulverized by a pulverizer. The resulting product was spun by a melt-spinning apparatus at 280° C., and drawn to form polyester filaments having brilliant yellow.

At the time of spinning and drawing, no filament breakage was observed.

COMPARATIVE EXAMPLE 2

Using POLIOTOL YELLOW 1090 set forth in Comparative Example 1, colored polyester filaments were prepared in the same way as in Example 43. The color of the filaments changed to greenish black.

What we claim is:

1. A compound of the formula

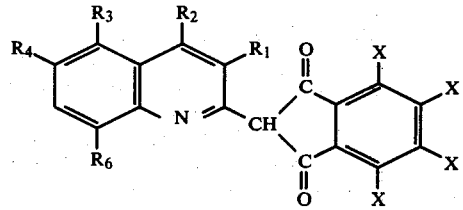

wherein $R_1$ and $R_2$, independently represent a hydrogen atom or a lower alkyl group having up to 5 carbon atoms; one $R_3$ or $R_4$ represents an imido group of the formula

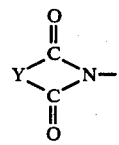

in which Y represents 1,2-phenylene group which is unsubstituted or is substituted by 1 to 4 halogen atoms, or a 1,2-, 2,3- or 1,8-naphthylene group which is unsubstituted or is substituted by 1 to 6 halogen atoms, and the other $R_3$ or $R_4$ represents a hydrogen atom; $R_6$ represents a hydrogen atom, a halogen atom, lower alkyl group having up to 5 carbon atoms or a lower alkoxy group having up to 5 carbon atoms; and X represents a halogen atom; with the proviso that when $R_3$ represents the imido group, $R_2$ represents a hydrogen atom.

2. The compound of claim 1 wherein $R_6$ is a chlorine or bromine atom.

3. A compound of claim 1 which is expressed by the formula

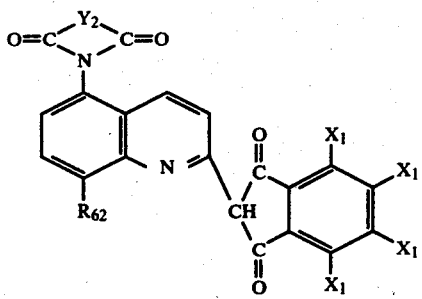 (I-e)

wherein $R_{62}$ represents a chlorine or bromine atom, an alkyl group having 1 to 3 carbon atoms, or an alkoxy group having 1 to 3 carbon atoms; $Y_2$ represents a 1,2-phenylene, 1,2-naphthylene, 2,3-naphthylene or 1,8-naphthylene group and $X_1$ is a chlorine or bromine atom.

4. A compound of claim 1 which is expressed by the formula

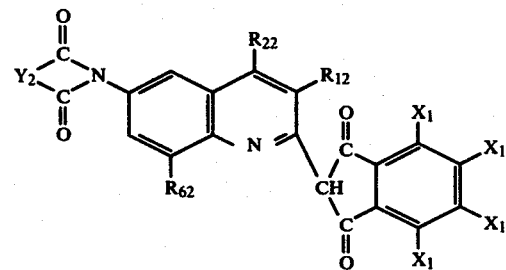 (I-f)

wherein $R_{12}$ and $R_{22}$, independently represent a hydrogen atom or an alkyl group having 1 to 3 carbon atoms; $R_{62}$ represents a chlorine or bromine atom, an alkyl group having 1 to 3 carbon atoms or an alkoxy group having 1 to 3 carbon atoms; $Y_2$ represents a 1,2-phenylene, 1,2-naphthylene, 2,3-nephthylene or 1,8-naphthylene group unsubstituted or substituted by 1 to 4 chlorine or bromine atoms; and $X_1$ represents a chlorine or bromine atom.

5. A compound of claim 1 which is expressed by the formula

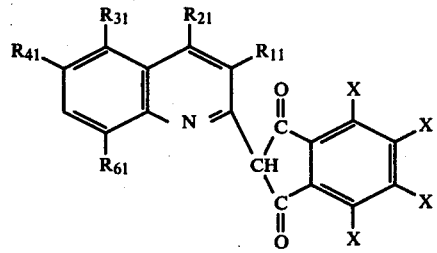

wherein $R_{11}$ and $R_{21}$, independently, represent a hydrogen atom or a lower alkyl group having up to 5 carbon atoms; one $R_{31}$ or $R_{41}$ represents an imido group of the formula

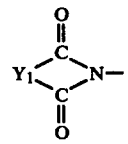

in which $Y_1$ represents a 1,2-phenylene, 1,2-naphthylene, 2,3-naphthylene or 1,8-naphthylene group which is unsubstituted or is substituted by 1 to 4 halogen atoms, and the other $R_{31}$ or $R_{41}$ represents a hydrogen atom; $R_{61}$ represents a halogen atom, a lower alkyl group having up to 5 carbon atoms or a lower alkoxy group having up to 5 carbon atoms; and X represents a halogen atom; with the proviso that when $R_{31}$ represents the imido group, $R_{21}$ represents a hydrogen atom.

* * * * *